(12) United States Patent
Park

(10) Patent No.: US 8,551,172 B2
(45) Date of Patent: Oct. 8, 2013

(54) INFLATABLE DISK IMPLANT

(76) Inventor: Kee B. Park, Wayne, NJ (US)

( * ) Notice: Subject to any disclaimer, the term of this patent is extended or adjusted under 35 U.S.C. 154(b) by 0 days.

(21) Appl. No.: 12/591,379

(22) Filed: Nov. 18, 2009

(65) Prior Publication Data
US 2010/0070032 A1  Mar. 18, 2010

Related U.S. Application Data

(62) Division of application No. 12/071,083, filed on Feb. 15, 2008, now abandoned.

(51) Int. Cl.
A61F 2/44 (2006.01)

(52) U.S. Cl.
USPC ........................................ 623/17.12

(58) Field of Classification Search
USPC .......................................... 623/17.11–17.16
See application file for complete search history.

(56) References Cited

U.S. PATENT DOCUMENTS

| | | | |
|---|---|---|---|
| 3,875,595 A | 4/1975 | Froning | |
| 5,549,679 A | 8/1996 | Kuslich | |
| 5,571,189 A | 11/1996 | Kuslich | |
| 5,674,295 A | 10/1997 | Ray et al. | |
| 6,048,343 A | 4/2000 | Mathis et al. | |
| 6,251,141 B1 | 6/2001 | Pierson, III et al. | |
| 6,331,179 B1 * | 12/2001 | Freid et al. | 606/279 |
| 6,375,682 B1 | 4/2002 | Fleischmann et al. | |
| 6,402,784 B1 | 6/2002 | Wardlaw | |
| 6,706,069 B2 | 3/2004 | Berger | |
| 6,852,095 B1 | 2/2005 | Ray | |
| 7,156,877 B2 | 1/2007 | Lotz et al. | |
| 2002/0147497 A1 | 10/2002 | Belef et al. | |
| 2003/0220649 A1 | 11/2003 | Bao et al. | |
| 2005/0149191 A1 * | 7/2005 | Cragg et al. | 623/17.11 |
| 2008/0262502 A1 * | 10/2008 | Ainsworth et al. | 606/99 |

* cited by examiner

Primary Examiner — Eduardo C Robert
Assistant Examiner — Ellen C Hammond
(74) Attorney, Agent, or Firm — Walter J. Tencza, Jr.

(57) ABSTRACT

A surgical implant for repairing an intervertebral disk. The implant includes an inflatable bladder and an externally threaded inlet port connected to the bladder. The inlet port has a threaded bore through which a filler is admitted into the bladder to inflate it. A setscrew is screwed into the threaded bore for plugging the threaded bore to retain the filler in the bladder.

6 Claims, 6 Drawing Sheets

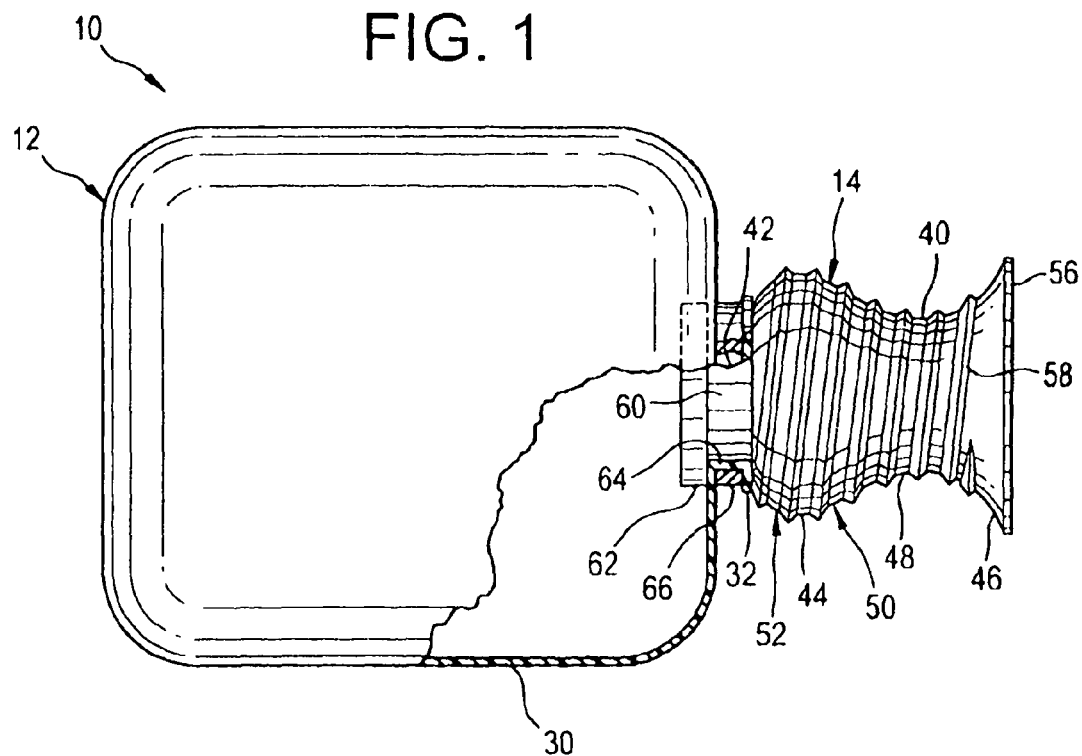
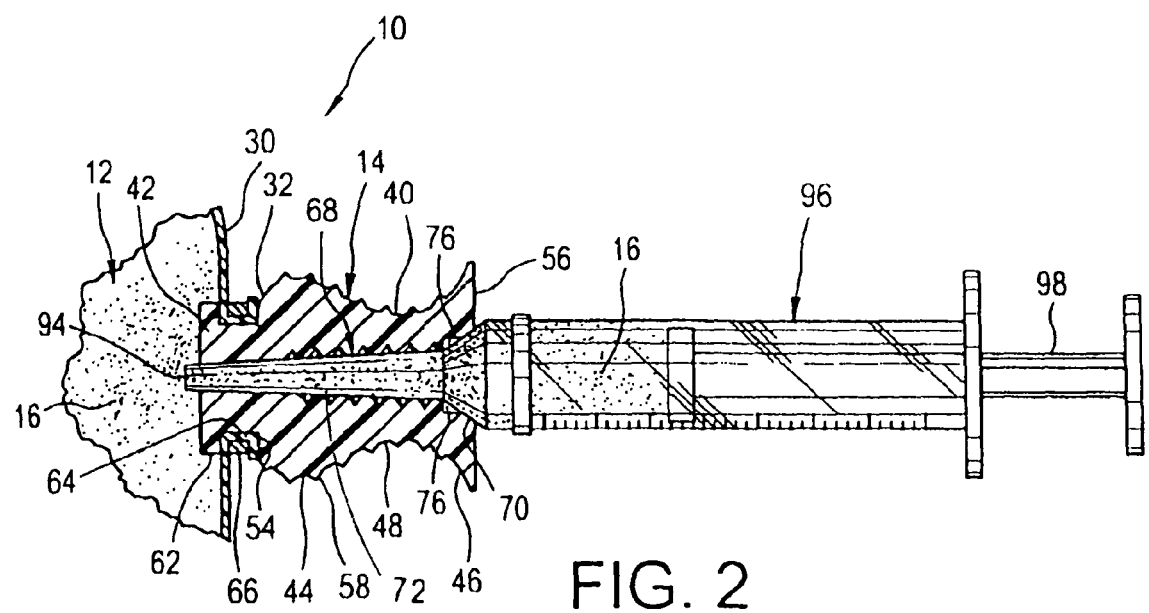

INFLATABLE DISK IMPLANT

CONTINUING APPLICATION DATA

This application is a division of U.S. patent application Ser. No. 12/071,083, filed on Feb. 15, 2008, now abandoned.

FIELD OF THE INVENTION

The present invention relates generally to a prosthesis or artificial body member that is implantable in a spinal column.

BACKGROUND OF THE INVENTION

Spinal nerve injuries can be the result of many things including torn, ruptured, prolapsed, or herniated intervertebral disks. These injuries occur when disks are damaged so that disk material (the nucleus pulposus) extrudes through the annulus fibrosis and compresses spinal nerves. For younger individuals, disk herniation can occur when lifting a heavy load whereas sneezing can cause disk herniation in the elderly. Regardless of cause, disk herniation is usually painful.

Common symptoms of disk herniation can include: a stiff neck, back aches, muscle spasms, pain while coughing or straining, and sensory disturbances in the arms, hands, legs and feet. Most disk herniation is treated conservatively, at least initially.

Conservative treatment consists of strict bed rest on a firm mattress and the use of drugs. Local heat applications are also employed, but prolonged heat applications increase the likelihood of congestion. Corsets can provide additional support for an individual with a lumbar disk problem.

When the conservative approach is ineffective, surgery may be required. Surgical treatment of a herniated intervertebral disk often involves the removal of all, or a portion, of the nucleus pulposus of an intervertebral disk. Currently, no reconstruction of an intervertebral disk is performed thereby allowing rapid degeneration of the disk. This invention allows reconstruction of the disk using an implant. For an effective treatment, however, an implant must be firmly anchored in place. Unfortunately, known implants have a tendency to shift around like the damaged intervertebral disks that they replace, resulting in surgical treatments whose long-term outcomes are not always positive. Implants that employ sutures as an anchor are notorious for their high failure rates. Other implant designs that rely on caps, covers, and tethers attached to the annulus fibrosis are similarly problematic.

SUMMARY OF THE INVENTION

In light of the problems associated with the known methods and apparatus for repairing ruptured, prolapsed, or herniated intervertebral disks, it is a principal object of the invention to provide a surgical implant that both replaces the nucleus pulposus of a human intervertebral disk and plugs the annulus fibrosis of the same disk. The means employed to replace the nucleus pulposus and the means employed to plug the annulus fibrosis serve to mutually anchor one another between adjacent vertebrae.

It is another object of the present invention to provide a surgical implant of the type described that can be easily embedded within the body of a patient with conventional surgical tools after a limited period of instruction.

It is an object of the invention to provide improved features and arrangements thereof in a surgical implant for the purposes described that is uncomplicated in construction, inexpensive to manufacture, and fully dependable in use.

Briefly, the surgical implant in accordance with this invention achieves the intended objects by featuring an inflatable bladder and an externally threaded inlet port connected to the inflatable bladder. The inlet port has a threaded bore through which a self-hardening, polymeric filler is admitted into the bladder to permanently inflate it. A setscrew is screwed into the threaded bore for plugging the threaded bore to retain the filler within the bladder.

The surgical implant constructed in accordance with the invention also features an inlet port having an "hourglass" shape with a peripheral groove near its midpoint for receiving the raised marginal edges of adjacent vertebrae to prevent the migration of the inlet port and the remainder of the implant of which the inlet port is a part. Furthermore, once positioned between adjacent vertebrae, the inlet port acts as a plug in the annulus fibrosis.

Additionally, the surgical implant features an inflatable bladder packed with a polymeric filler that assumes the shape of an intervertebral void to anchor the inlet port for the inflatable bladder located between adjacent vertebrae.

Furthermore, the surgical implant features an inlet port made of an elastomeric material and having a threaded bore therein for the passage of polymeric filler into the inflatable bladder. The threaded bore is plugged by an oversized, tapered setscrew that expands the inlet port to lock such tightly between adjacent vertebrae.

The foregoing and other objects, features and advantages of the present invention will become readily apparent upon further review of the following detailed description of the preferred embodiments as illustrated in the accompanying drawings.

BRIEF DESCRIPTION OF THE DRAWINGS

The present invention may be more readily described with reference to the accompanying drawings, in which:

FIG. 1 is a side view of a surgical implant in accordance with the present invention with portions broken away to reveal details thereof.

FIG. 2 is a longitudinal cross-sectional view of the inlet port of the surgical implant of FIG. 1 with a syringe inserted therein.

Similar reference characters denote corresponding features consistently throughout the accompanying drawings.

DETAILED DESCRIPTION OF THE PREFERRED EMBODIMENTS

Figure 3:
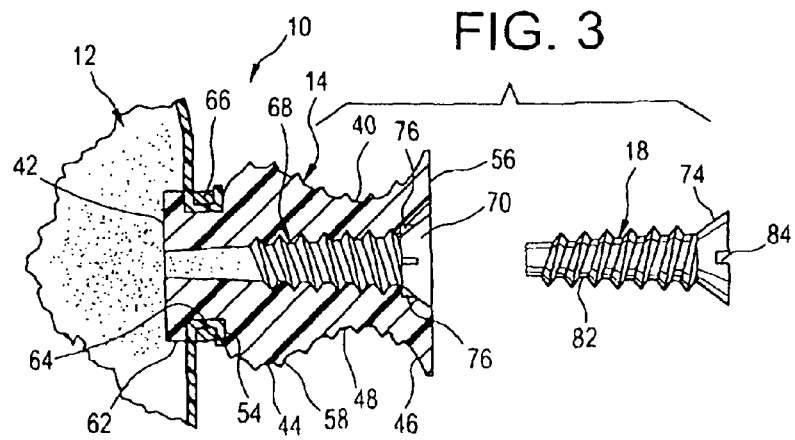
FIG. 3 is a longitudinal cross-sectional view of the inlet port with a setscrew being inserted therein.

Referring now to the figures, a surgical implant in accordance with the present invention is shown at 10 in FIGS. 1-9. Implant 10 includes an inflatable bladder 12 to which is fastened an inlet port 14 for the controlled admission of a filler 16 into bladder 12. A setscrew 18 plugs inlet port 14 to retain filler 16 within bladder 12. In use, implant 10 partially replaces an intervertebral disk 20 having an outer annulus fibrosis 22 and an inner nucleus pulposus 24. Implant 10 permits flexible articulation of adjacent vertebrae 26 and 28 yet provides an internal resistance to bending that lends stability to a spine.

Inflatable bladder 12 includes a material-holding reservoir 30 from which a tubular spout 32 extends. Reservoir 30 and spout 32 are integrally formed of a plastic material that is lightweight, nonporous, impermeable, and biocompatible but incapable of dissolution within the human body. Similarly, the material is flexible and strong so that it cannot be easily torn or punctured when used. Bladder 12 can be formed from any suitable material and made in any suitable manner known in the art.

Reservoir 30 is provided with a size and shape that is substantially the same as that of intervertebral void 34 left after excavating the nucleus pulposus 24 between vertebrae 26 and 28. When inflated by the addition of filler 16 to the interior of bladder 12, reservoir 30 completely packs void 34 and fully engages the surfaces that define the boundaries of void 34 such as the layers of cartilage 36 and 38 covering the upper and lower surfaces of vertebrae 26 and 28 and the annulus fibrosis 22. Furthermore, inflated reservoir 30 drives vertebrae 26 and 28 away from one another and retains such in a spaced-apart condition to lengthen and tighten the fibers of annulus fibrosis 22 resulting in spinal stability.

Filler 16 is a biocompatible polymer, delivered to the interior of bladder 12 in a liquid or semi-liquid state, which is capable of gelling within a short period of time. Once solidified, the polymer must stay as a gel for the lifetime of the patient. One suitable polymer is formed by the mixture of bovine serum albumin (BSA) and glutaldehyde that hardens from a liquid to a rubber-like solid within minutes. Of course, other materials can be employed as filler 16 and these can be provided in a suitable manner to the interior of bladder 12 in a solid, liquid, and/or gaseous state.

Inlet port 14 is a tube having inner and outer diameters that vary along the length thereof. One end of inlet port 14 is formed as a vertebral engagement portion 40 with a silhouette resembling that of an hourglass. The other end of inlet port 14 is a bladder attachment portion 42 with a T-shaped outline.

Vertebral engagement portion 40 has a hip 44 and a shoulder 46 connected together by a narrow waist 48. As shown, hip 44 is convex with an inwardly sloping surface 50 that cants toward waist 48 and an outwardly sloping surface 52 that tilts away from waist 48 and toward the inner end 54 of vertebral engagement portion 40. Inwardly sloping surface 50 flows smoothly into waist 48 that is concave and defines a peripheral groove about the middle of vertebral engagement portion 40. Waist 48, in turn, flows smoothly into shoulder 46 that flares outwardly from waist 48 to terminate at the planar outer end 56 of vertebral engagement portion 40.

Helical threads 58 are provided around the periphery of vertebral engagement portion 40 extending from inner end 54 to outer end 56. Threads 58 have an even height and width along their lengths and conform closely to the surface contours of vertebral engagement portion 40. Thus, threads 58 trace helical paths that increase in diameter over outwardly sloping surface 52 when traveling from inner end 54 toward outer end 56. Also, threads 58 trace helical paths that decrease in diameter over inwardly sloping surface 50 to the middle of waist 48. From the middle of waist 48 across to shoulder 46, the helical paths of threads 58 increase in diameter.

Attachment portion 42 extends from inner end 54 of vertebral engagement portion 40 and is sized for positioning within spout 32 of bladder 12. Attachment portion 42 includes a cylindrical leg 60 from the bottom of which a peripheral flange 62 extends outwardly. A peripheral channel 64 is formed between peripheral flange 62 and inner end 54 of vertebral engagement portion 40.

After inserting attachment portion 42 of inlet port 14 into spout 32 of bladder 12, a locking ring 66 is fitted around spout 32 and over attachment portion 42 at a location adjacent peripheral channel 64. Since locking ring 66 is dimensioned to fit snugly within peripheral channel 64, the release of locking ring 66 forces spout 32 against attachment portion 42 and strongly fastens inlet port 14 to bladder 12. Preferably, locking ring 66 is formed from a resilient plastic material that permits it to be stretched prior to it being seated in peripheral channel 64.

A bore 68 extends longitudinally through inlet port 14, passing through both vertebral engagement portion 40 and attachment portion 42. Bore 68 has an inlet end 70 in shoulder 46 and a threaded outlet end 72 that extends from waist 48 to flange 62, both ends 70 and 72 taper in diameter. Preferably, inlet end 70 is enlarged in terms of diameter so that the tapered head 74 of setscrew 18 can be countersunk therein. Inlet end 70 is also provided with a plurality of radial slots 76 around the perimeter thereof. The tool end 78 of a screwdriver 80 can be positioned within slots 76 for rotating inlet port 14 so as to screw it into intervertebral void 34.

Setscrew 18 is adapted to be threaded into bore 68. Setscrew 18 has a tapered head 74 for positioning in inlet end 70 of bore 68 and a threaded rod 82 extending from head 74 for positioning within threaded outlet end 72 of bore 68. Head 74 is provided with a plurality of radial slots 84 that receive tool end 78 of screwdriver 80 when it is desired to thread setscrew 18 into bore 68. For a snug fit in bore 68, both head 74 and threaded rod 82 are tapered like bore 68.

Inlet port 14 is formed from a resilient plastic material and bore 68 is provided with a size that is slightly smaller in terms of diameter than that of setscrew 18. Thus, when setscrew 18 is threaded into bore 68, setscrew 18 acts as a wedge to expand inlet port 14, increasing its outer diameter to firmly anchor such between vertebrae 26 and 28.

Figure 4:
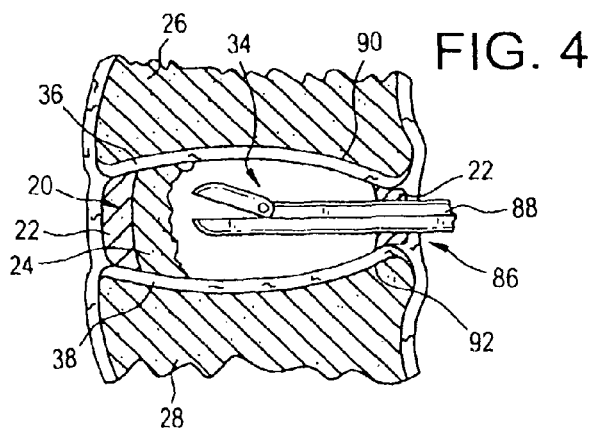
FIG. 4 is a schematic cross-sectional showing forceps being employed to remove the nucleus pulposus of an intervertebral disk.
Figure 5:
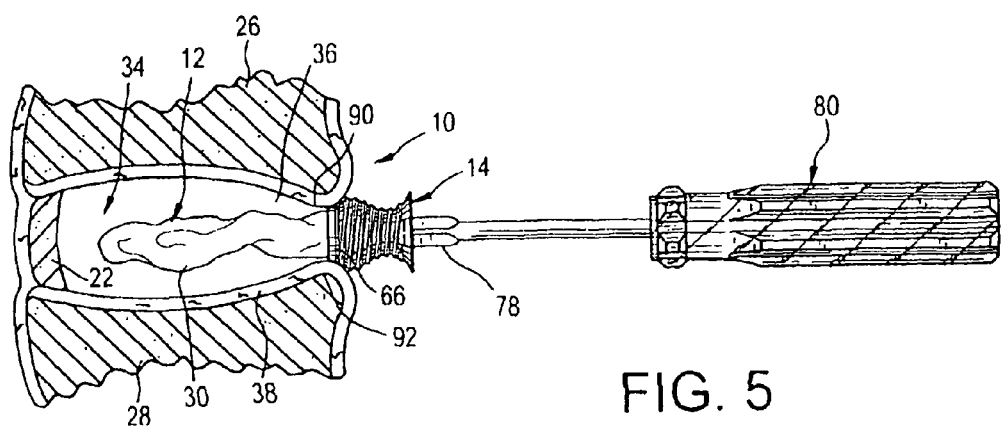
FIG. 5 is a schematic cross-sectional showing the surgical implant, with its inflatable bladder in a collapsed state, positioned by a screwdriver for insertion between adjacent vertebrae.

The use of surgical implant 10 is straightforward. First, through an incision 86 in annulus fibrosis 22, damaged nucleus pulposus 24 is removed from between vertebrae 26 and 28 with forceps 88 as shown in FIG. 4. Then, as is illustrated in FIG. 5, deflated bladder 12 is inserted into the intervertebral void 34 resulting from the removal of nucleus pulposus 24. Simultaneously, inner end 54 is placed against incision 86. Now, by positioning tool end 78 of screwdriver 80 into end 70 of bore 68 and into slots 76, with continued reference to FIG. 5, inlet port 14 is ready to be screwed into void 34.

Figure 6:
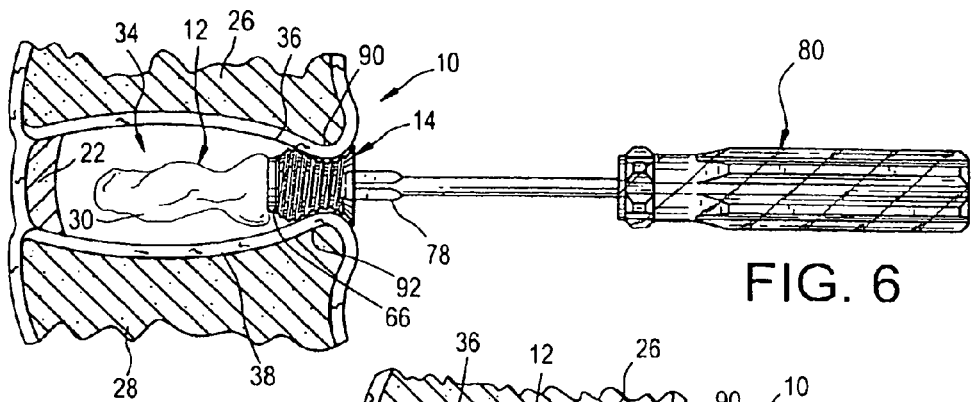
FIG. 6 is a schematic cross-sectional view showing the surgical implant, with its inflatable bladder in a collapsed state, after being driven between adjacent vertebrae with the upper and lower surfaces of the vertebrae pinching the inlet port of the implant to hold such in place.

Threads 58 on intervertebral engagement portion 40 facilitate the entry of inlet port 14 into void 34. As screwdriver 80 is turned, the portion of threads 58 adjacent outwardly sloping surface 52 serve to lead inlet port 14 through incision 86, grip and spread vertebrae 26 and 28, and pull inlet port 14 forward into void 34. The portion of threads 58 adjacent inwardly sloping surface 50, waist 48, and shoulder 46, aid in setting waist 48 comfortably between raised marginal edges 90 and 92 of vertebrae 26 and 28 as shown in FIG. 6. The threads 58 adjacent waist 48 "bite" into marginal edges 90 and 92 to securely anchor inlet port 14 in place with flared shoulder 46 effectively plugging incision 86.

Figure 7:
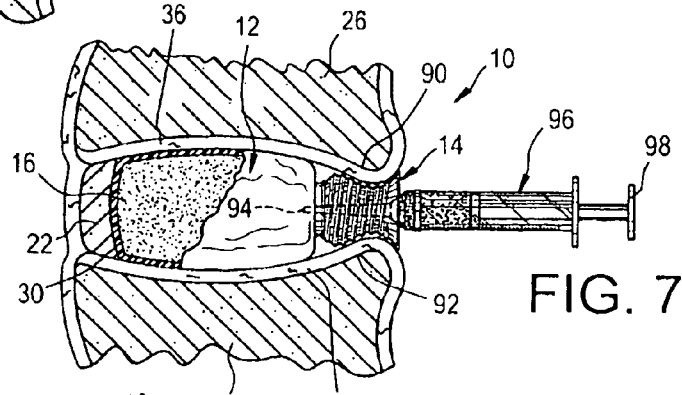
FIG. 7 is a schematic cross-sectional view showing the inflatable bladder of the surgical implant, positioned between adjacent vertebrae, being filled with a settable polymer delivered through the inlet port by a syringe.

Once inlet port 14 is positioned between vertebrae 26 and 28, bladder 12 is inflated. To do this, the nozzle 94 of a syringe 96, filled with a liquid or semi-liquid polymer filler 16, is inserted into bore 68 as shown in FIGS. 2 and 7. Preferably, nozzle 94 is provided with a taper like that of bore 68 so that upon insertion, a good seal is provided to prevent leakage of filler 16. Then, plunger 98 of syringe 96 is depressed to drive a predetermined volume of filler 16 into bladder 12. The pressure applied to plunger 98 and ultimately to filler 16 is largely a matter of trial and error but must be sufficient to expand reservoir 30 so that it packs intervertebral void 34 and holds vertebrae 26 and 28 in a spaced-apart condition to lengthen and tighten the fibers of annulus fibrosis 22.

Figure 8:
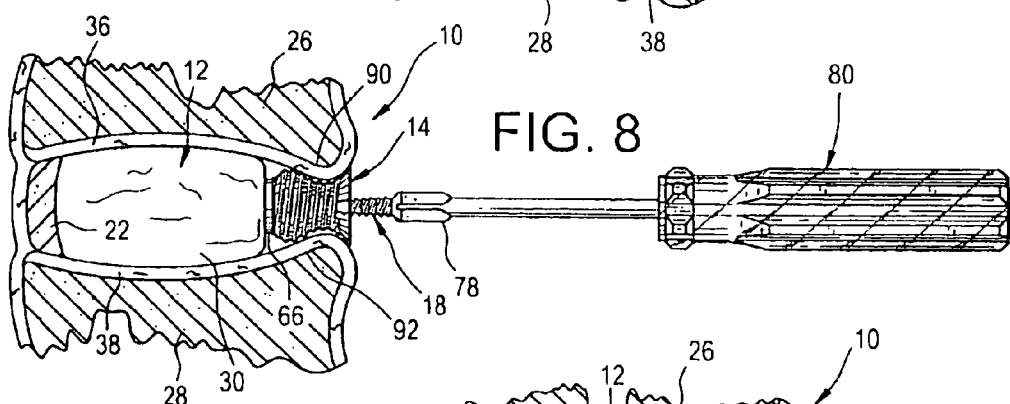
FIG. 8 is a schematic cross-sectional view showing a setscrew being threaded into the inlet port of the surgical implant, positioned between adjacent vertebrae, by a screwdriver to retain a settable polymer within the inflatable bladder of the implant.
Figure 9:
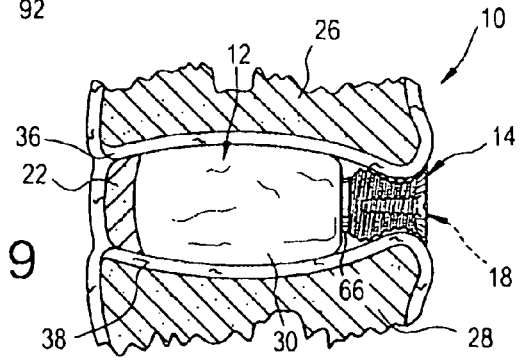
FIG. 9 is a schematic cross-sectional view showing the surgical implant fully deployed between adjacent vertebrae.
Figure 10:
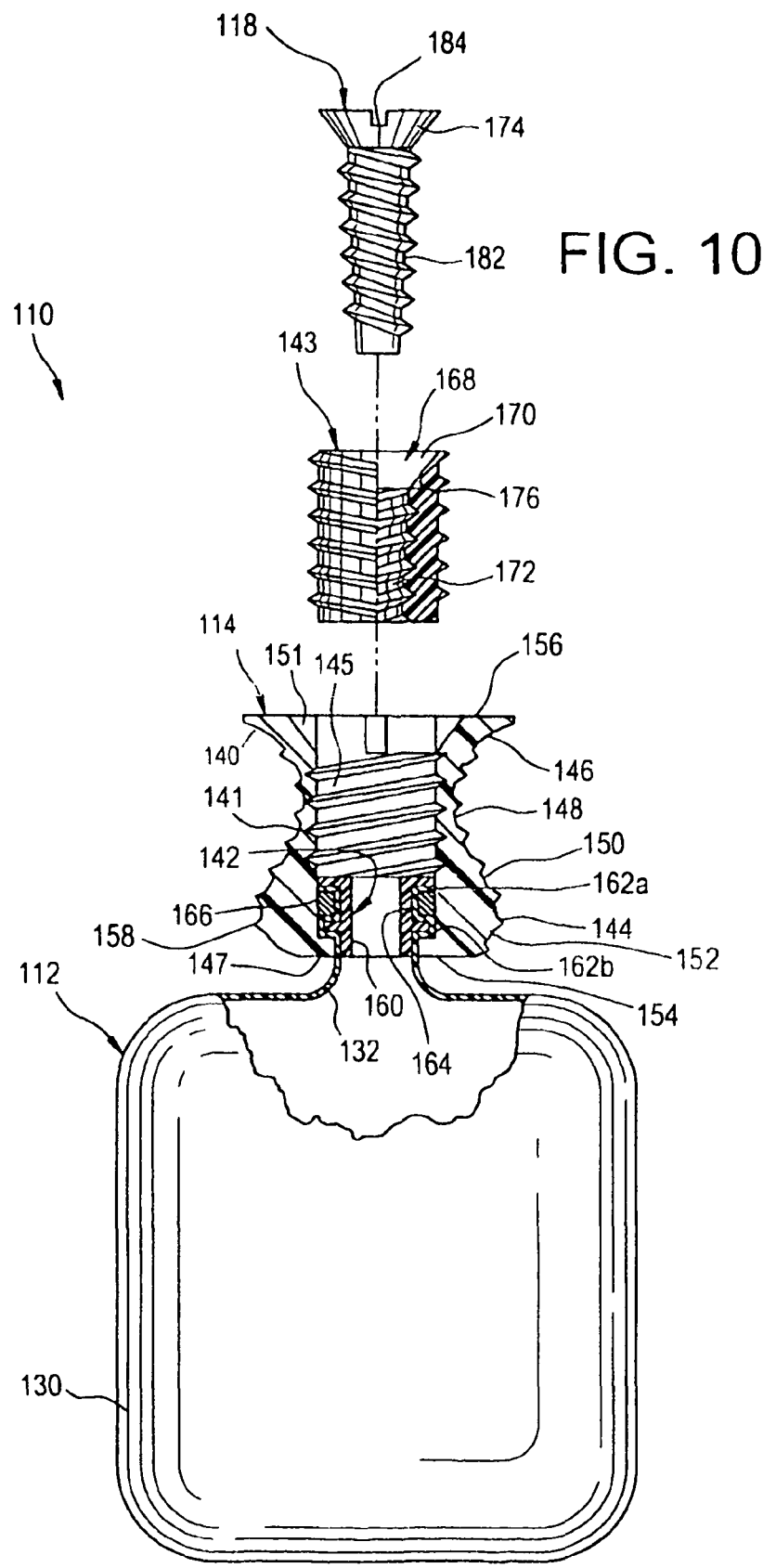
FIG. 10 is an exploded side view of an alternative surgical implant in accordance with the present invention with portions broken away to reveal details thereof.

After polymeric filler 16 has changed state from a liquid or semi-liquid to a rubber-like solid (a few minutes), nozzle 94 is withdrawn from bore 68 and is replaced by setscrew 18. FIG. 8 illustrates screwdriver 80 engaged with head 74 of setscrew 18 and threading setscrew 18 into bore 68. Because setscrew 18 is somewhat larger than bore 68 and inlet port 14 is formed of a resilient material, fully threading setscrew 18 into bore 68 in accordance with FIG. 9 slightly enlarges the diameter of inlet port 14 to lock such in place between vertebrae 26 and 28. Finally, after a brief period of convalescence, the patient receiving surgical implant 10 should find his spine to be pain free with nearly full mobility restored.

An alternative surgical implant in accordance with the present invention is shown at 110 in FIGS. 10-16. Implant 110 includes an inflatable bladder 112 to which is fastened an inlet port 114 for the controlled admission of a filler 116, identical to filler 16 described above, into bladder 112. A setscrew 118 plugs inlet port 114 to retain filler 116 within bladder 112.

Figure 11:
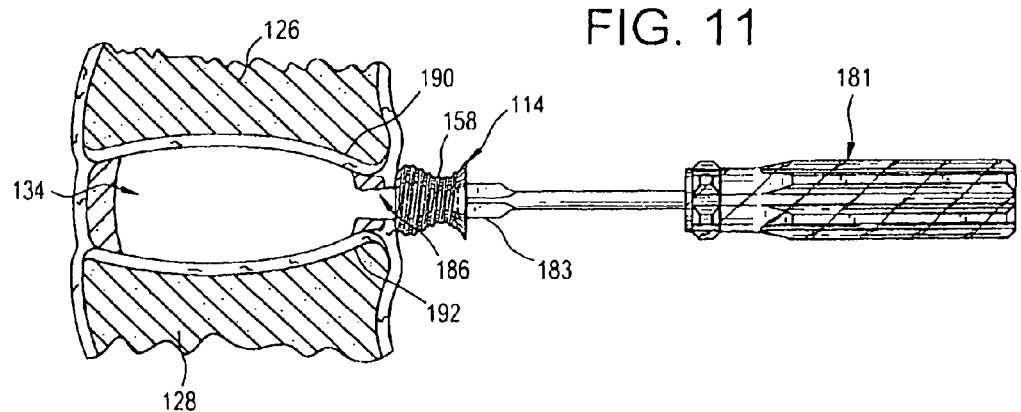
FIG. 11 is a schematic cross-sectional showing the inlet port of the surgical implant of FIG. 10 being positioned by a screwdriver for insertion between adjacent vertebrae.

Inflatable bladder 112 includes a material-holding reservoir 130 from which a tubular spout 132 extends. Reservoir 130 and spout 132 are integrally formed from the same materials and same manner as reservoir 30 and spout 32 of bladder 12. Reservoir 130 is provided with a size and shape that is substantially the same as that of intervertebral void 134 left after excavating the nucleus pulposus from between a pair of adjacent vertebrae 126 and 128 as shown in FIG. 11. When inflated by the addition of filler 116 to the interior of bladder 112, reservoir 130 packs void 134 and fully engages the surfaces that define the boundaries of void 134. Furthermore, inflated reservoir 130 forces vertebrae 126 and 128 apart and retains such in a spaced-apart condition to lengthen and tighten the fibers of annulus fibrosis 122.

Inflatable bladder 112 further comprises an attachment portion 142 that is inserted within spout 132 and a locking ring 166 that is fitted over spout 132. Attachment portion 142 includes a cylindrical leg 160 from the top and middle of which peripheral flanges 162a and 162b extend outwardly. A peripheral channel 164 is formed between peripheral flanges 162a and 162b. After inserting attachment portion 142 into spout 132, locking ring 166 is moved over spout 132 and attachment portion 142 to a location adjacent peripheral channel 164. Since locking ring 166 is dimensioned to fit snugly within peripheral channel 164, the release of locking ring 166 forces spout 132 against attachment portion 142 and strongly fastens attachment portion 142 to bladder 112.

Inlet port 114 includes a vertebral engagement portion 140 having a tubular sleeve 141 with a silhouette resembling that of an hourglass and a tubular insert 143 for positioning within sleeve 141. Sleeve 141 has a hip 144 and a shoulder 146 connected together by a narrow waist 148. Hip 144 is convex with an inwardly sloping surface 150 that cants toward waist 148 and an outwardly sloping surface 152 that tilts away from waist 148 and toward the inner end 154 of sleeve 141. Inwardly sloping surface 150 flows smoothly into waist 148 that is concave and defines a peripheral groove about the middle of sleeve 141. Also, waist 148 flows smoothly into shoulder 146 that flares outwardly from waist 148 to terminate at the planar outer end 156 of sleeve 141.

Helical threads 158 are provided around the periphery of sleeve 141 extending between ends 154 and 156. Threads 158 have an even height and width along their lengths and conform closely to the surface contours of sleeve 141. Threads 158, therefore, trace helical paths that increase in diameter over outwardly sloping surface 152 when moving from end 154 toward end 156. Additionally, threads 158 trace helical paths that decrease in diameter over inwardly sloping surface 150 to the middle of waist 148. From the middle of waist 148 to shoulder 146 the helical paths of threads 158 increase in diameter.

A threaded bore 145 extends longitudinally through tubular sleeve 141 and is sized to receive attachment portion 142 of bladder 112 and tubular insert 143. Sleeve 141 is provided with a peripheral lip 147 at inner end 154 that projects inwardly into bore 145. Lip 147 serves as an abutment surface for attachment portion 142 and a stop to prevent the full passage of both attachment portion 142 and insert 143 through sleeve 141.

Tubular insert 143 has helical threads 149 on its exterior so that it can be screwed into threaded bore 145 in tubular sleeve 141. A threaded bore 168 also extends longitudinally through tubular insert 143 so that setscrew 118 can be screwed into it. Bore 168 has an inlet end 170 for positioning adjacent shoulder 146 and a threaded outlet end 172 for positioning adjacent waist 148, both ends 170 and 172 tapering in diameter. Preferably, inlet end 170 is enlarged so that the tapered head 174 of setscrew 118 can be countersunk within it. Inlet end 170 is also provided with a plurality of radial slots 176 around its perimeter. The tool end 178 of a screwdriver 180 can be positioned within slots 176 for rotating insert 143 so as to screw it into sleeve 141. Continued rotation of screwdriver 180, once insert 143 is fully screwed into sleeve 141, imparts rotational motion to sleeve 141 to screw inlet port 114 into intervertebral void 134.

Setscrew 118 is threaded into bore 168 in tubular insert 143. Setscrew 118 has a head 174 for positioning in inlet end 170 of bore 168 and a threaded rod 182 extending from head 174 for positioning within threaded outlet end 172 of bore 168. Head 174 is provided with a plurality of radial slots 184 that receive the tool end 178 of screwdriver 180 when it is desired to thread setscrew 118 into bore 168. For a snug fit within bore 168, head 174 and threaded rod 182 are provided with tapers similar to that of bore 168.

Tubular sleeve 141 and tubular insert 143 are formed from a resilient plastic material and bore 168 is provided with a size that is slightly smaller in terms of diameter than that of setscrew 118. Thus, when setscrew 118 is threaded into bore 168, setscrew 118 acts as a wedge to expand insert 143 and sleeve 141, increasing the outer diameter of inlet port 114 to firmly anchor such between vertebrae 126 and 128.

The use of alternative surgical implant 110 is as straightforward as the use of surgical implant 10. First, through an incision 186 in annulus fibrosis 122, damaged nucleus pulposus is removed from between vertebrae 126 and 128 with forceps as shown in FIG. 4 to form intervertebral void 134. Then, as illustrated in FIG. 11, inner end 154 of sleeve 141 is placed against incision 186 by means of screwdriver 181 whose tool end 183 is inserted within radial slots 151 provided in outer end 156 of sleeve 141 about threaded bore 145. Now, by apply a light pressure to screwdriver 181 and by rotating screwdriver 181, sleeve 141 is screwed between vertebrae 126 and 128 into void 134 at the location shown in FIG. 12.

Figure 12:
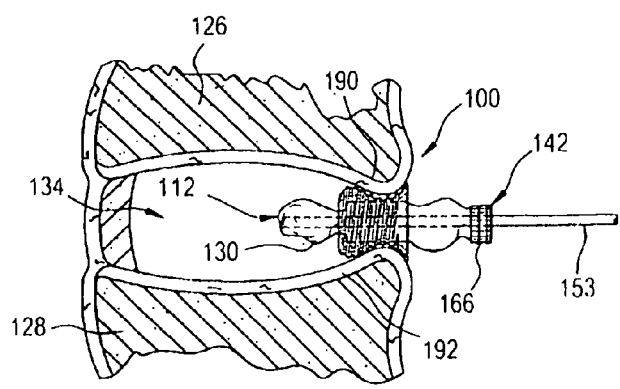
FIG. 12 is a schematic cross-sectional view showing the inlet port of the alternative surgical implant pinched between the upper and lower surfaces of adjacent vertebrae with the inflatable bladder of the alternative implant being slid through the inlet port into the evacuated space between the vertebrae.

Threads 158 on sleeve 141 facilitate the entry of sleeve 141 into void 134. As screwdriver 181 is turned, the portion of threads 158 adjacent outwardly sloping surface 152 serve to: lead sleeve 141 through incision 186, grip and spread vertebrae 126 and 128, and pull sleeve 141 forward into void 134. The portions of threads 158 adjacent inwardly sloping surface 150, waist 148, and shoulder 146, aid in setting waist 148 comfortably between raised marginal edges 190 and 192 of vertebrae 126 and 128 as shown in FIG. 12. The threads 158 adjacent waist 148 "bite" into marginal edges 190 and 192 of vertebrae 126 and 128 to securely anchor sleeve 141 in place with shoulder 146 effectively plugging incision 186.

Figure 13:
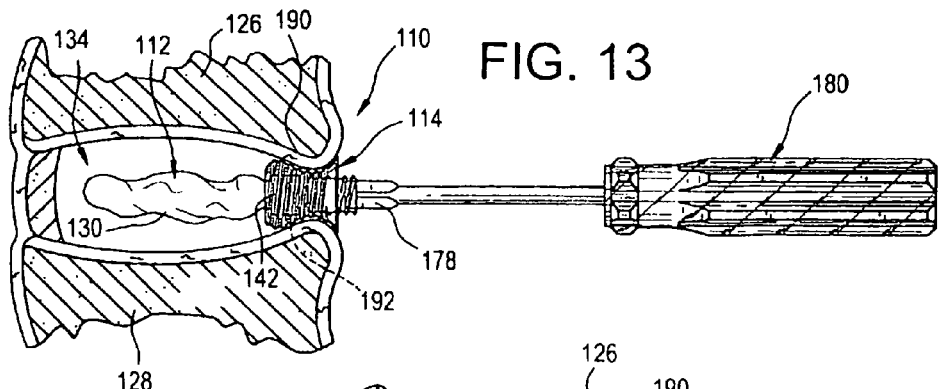
FIG. 13 is a schematic cross-sectional view showing the locking sleeve of the alternative surgical implant being screwed into the inlet port, pinched between the upper and lower surfaces of adjacent vertebrae, to fasten the inflatable bladder to the inlet port.

Once sleeve 141 is positioned between vertebrae 126 and 128, bladder 112 is affixed to sleeve 141. To do this a rod 153 is inserted through attachment portion 142 into reservoir 130 as shown in FIG. 12, and rod 153, with bladder 112 positioned thereon, is extended through bore 145 in sleeve 141 into void 134. Then, when attachment portion 142 is engages lip 147, rod 153 is withdrawn from bore 145 leaving bladder 112 in place in void 134. Next, as illustrated in FIG. 13, tubular insert 143 is threaded into bore 145 by positioning tool end 178 of screwdriver 180 in slots 176 and rotating screwdriver 180. When insert 143 presses against attachment portion 142 rotation of screwdriver 180 is stopped and screwdriver 180 is withdrawn from slots 176. Bladder 112 and inlet port 114 cannot now be easily separated.

Figure 14:
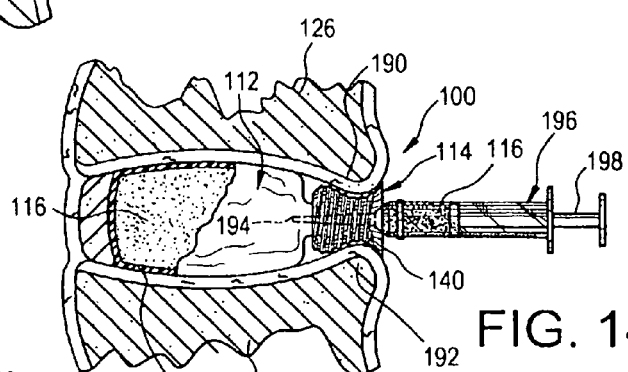
FIG. 14 is a schematic cross-sectional view showing the inflatable bladder of the alternative surgical implant, positioned between adjacent vertebrae, being filled with a settable polymer delivered through the inlet port by a syringe.

Bladder 112 is inflated by pressing the nozzle 194 of a syringe 196, filled with a liquid or semi-liquid polymer filler 116, into bore 168 in insert 143 as shown in FIG. 14. Nozzle 194 is tapered like bore 168 so that upon insertion into bore 168, a good seal is provided. Then, plunger 198 of syringe 196 is depressed to drive polymeric filler 116 into bladder 112 to expand reservoir 130 so that it packs intervertebral void 134 and holds vertebrae 126 and 128 in a spaced-apart condition.

Figure 15:
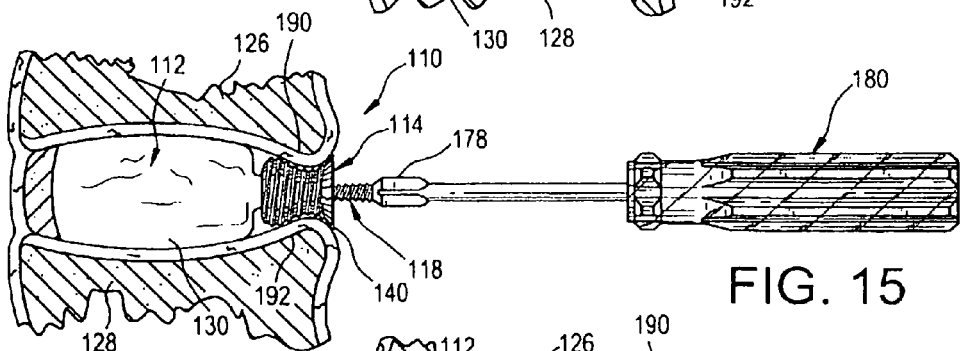
FIG. 15 is a schematic cross-sectional view showing a setscrew being threaded into the inlet port of the alternative surgical implant, positioned between adjacent vertebrae, by a screwdriver to retain a settable polymer within the inflatable bladder of the implant.
Figure 16:
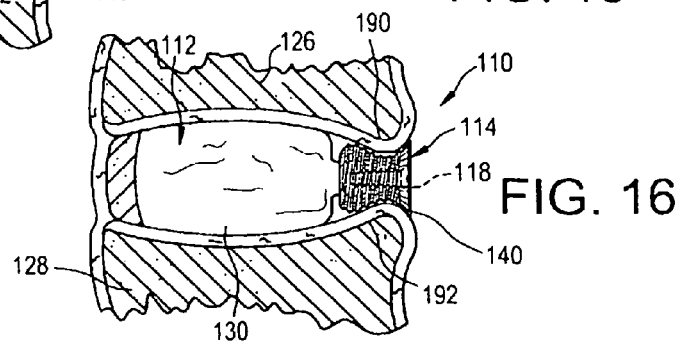
FIG. 16 is a schematic cross-sectional view showing the alternative surgical implant fully deployed between adjacent vertebrae.

After filler 116 has hardened, nozzle 194 is withdrawn from bore 168 and is replaced by setscrew 118 as shown in FIG. 15. Here, the tool end 178 of screwdriver 180 is positioned within slots 184 in setscrew 118 and is rotated to thread setscrew 118 into bore 168. Because setscrew 118 is somewhat larger than bore 168 and sleeve 141 and insert 143 are formed of a resilient material, fully threading setscrew 118 into bore 168 in accord with FIG. 16 increases the diameter of inlet port 114 to lock inlet port 114 between vertebrae 126 and 128. After convalescing, the patient should find that he is pain free and his spine has a full range of flexible articulation.

While surgical implants 10 and 110 have been described with a high degree of particularity, it will be appreciated by those skilled in the art that modifications can be made to them. Thus, it is to be understood that the present invention is not limited to the implant embodiments described above, but encompasses any and all embodiments within the scope of the following claims.

I claim:

1. A surgical implant, comprising:
an inflatable bladder;
an inlet port being affixed to said bladder, said inlet port having a first threaded bore through which a filler can be admitted into said bladder to inflate same, said inlet port being externally threaded, and said inlet port being provided with a peripheral groove around the middle thereof for receiving therein the raised marginal edges of a pair of adjacent vertebrae;
a setscrew being threadably positioned within said first threaded bore for closing said first threaded bore; and,
a filler being positioned within said inflatable bladder for inflating same.

2. The surgical implant according to claim 1 wherein said inlet port includes:
an inner end and an outer end remote from said inner end;
a convex hip being positioned adjacent to said inner end, said convex hip having an outwardly sloping surface tilting toward said inner end and an inwardly sloping surface canting away from said inner end;
a concave waist being connected to said inwardly sloping surface of said convex hip; and,
a shoulder being positioned adjacent to said outer end and being connected to said concave waist, and said shoulder flaring outwardly from said waist.

3. The surgical implant according to claim 1 wherein said inlet port is provided with a plurality of radial slots about said first threaded bore for screwing said surgical implant into an intervertebral void.

4. The surgical implant according to claim 1 wherein said inlet port is formed from a resilient material and said setscrew is tapered and is oversized with respect to said first threaded bore so as to serve as a wedge when screwed into said first threaded bore that enlarges the diameter of said inlet port.

5. The surgical implant according to claim 1 wherein said inflatable bladder includes a material-holding reservoir from which a tubular spout extends and said inlet port includes a peripheral channel at one end thereof, and said surgical implant further comprises a locking ring being positioned about said tubular spout and within said peripheral channel for connecting said inflatable bladder to said inlet port.

6. The surgical implant according to claim 1 wherein said filler is a polymeric gel.

* * * * *